United States Patent
Yan et al.

(10) Patent No.: US 8,618,504 B2
(45) Date of Patent: Dec. 31, 2013

(54) LIGHT SOURCE APPARATUS FOR FLUORESCENCE PHOTOGRAPHY

(75) Inventors: Shuo-Ting Yan, Hsin-Chu (TW); Wei-Li Hong, Hsin-Chu (TW); Yuan Yu Tsai, legal representative, Hsin-Chu (TW)

(73) Assignee: Yayatech Co., Ltd., Hsinchu (TW)

( * ) Notice: Subject to any disclaimer, the term of this patent is extended or adjusted under 35 U.S.C. 154(b) by 435 days.

(21) Appl. No.: 12/914,341

(22) Filed: Oct. 28, 2010

(65) Prior Publication Data

US 2012/0001095 A1   Jan. 5, 2012

(30) Foreign Application Priority Data

Jun. 30, 2010   (TW) .............................. 99121430 A

(51) Int. Cl.
*F21V 9/16*   (2006.01)
(52) U.S. Cl.
USPC ....................................................... 250/458.1
(58) Field of Classification Search
USPC ....................................................... 250/458.1
See application file for complete search history.

(56) References Cited

U.S. PATENT DOCUMENTS

| | | | |
|---|---|---|---|
| 2006/0030026 A1* | 2/2006 | Garcia | 435/287.1 |
| 2008/0179539 A1* | 7/2008 | Rasnow et al. | 250/458.1 |
| 2010/0075408 A1 | 3/2010 | Waiche et al. | |

FOREIGN PATENT DOCUMENTS

| | | |
|---|---|---|
| CN | 2560943 Y | 7/2003 |
| CN | 1595105 A | 3/2005 |
| CN | 101724683 A | 6/2010 |
| JP | 2007-333479 | * 12/2007 |

\* cited by examiner

*Primary Examiner* — David Porta
*Assistant Examiner* — Edwin Gunberg
(74) *Attorney, Agent, or Firm* — Rosenberg, Klein & Lee

(57) ABSTRACT

A light source apparatus for fluorescence photography of biomolecule sample gels is disclosed. The light source apparatus comprises a housing, a transparent plate disposed in a light transmission zone at the top of the housing, and at least one LED array disposed in the housing out of the range of the light transmission zone. The LED array irradiates obliquely to the light transmission zone for preventing the light spots from interfering in the observation. Each of LED array may comprises different colors of LEDs for different biomolecule samples.

7 Claims, 2 Drawing Sheets

LIGHT SOURCE APPARATUS FOR FLUORESCENCE PHOTOGRAPHY

BACKGROUND OF THE INVENTION

The present invention relates to a light source apparatus for fluorescence photography, and more particularly to a light source apparatus for fluorescence photography of biomolecule sample gels.

In biotechnology experiments, to all eukaryotes, protein phosphorylation can cause the organism to change the activation of the intracellular protein or enzyme, transmit signal, or regulate cell physiological processes such as cell metabolism, cell growth, cell proliferation or cell cancerization. However, the content of phosphorylated proteins in organism is extremely low and normally kept in a dynamic balance status. It is difficult to detect or analyze the phosphorylated proteins before pre-concentration process.

Western blotting was introduced by Towbin et. al. in 1979 and is now a routine technique for protein analysis. The specificity of the antibody-antigen interaction enables a target protein to be identified in the midst of a complex protein mixture. The biomolecule sample that is separated by gel electrophoresis is labeled with an enzyme or fluorescent dye for qualitative or quantitative analysis.

According to the characteristics of biomolecule samples, different enzymes or fluorescent dyes are used to label the biomolecule samples. After sample labeling, the method for observation is also different. For example, in a DNA fluorescence image observation, a 465 nm blue LED-based backlight is used to excite the labeled DNA sample to fluoresce, and then an optical lens and a CCD camera are used for observation or photographing.

FIG. 1 illustrates fluorescence photographing apparatus in accordance with a prior art. As illustrated, the fluorescence photographing apparatus 10 comprises a photography module 12, an amber filter 141 and a light source module 18.

The light source module 18 comprises a housing 181 having a top opening, a blue filter 187 mounted in the top opening of the housing 181 and a blue LED array 183 disposed in the housing 181 below the top opening. After gel phosphoresis, the DNA gel 16 can be placed on the blue filter 187.

The blue LED array 183 provides a blue light source for exciting the sample. The blue filter 187 allows only blue light with 465 nm wavelength to pass. The DNA in the DNA gel 16 is excited to fluoresce and is able to be observed or photographed by means of the photography module 12.

To enhance the image contrast, an amber filter 141 may be disposed between the photography module 12 and the DNA gel 16 to remove the blue light of the back light source. Further, in order to prevent light spots of the LED light source from interfering in the image, a diffuser is disposed between the blue LED array 183 and the blue filter 187 for diffusing each light spot into a uniform light in a larger area.

The aforesaid fluorescence photography apparatus in accordance with a prior art is workable for fluorescence photographing and observation. However, due to structural limitation, one apparatus is suitable for exciting light source with single wavelength. Furthermore, the diffuser 185 in the light source module 18 will reduce the intensity of the exciting light source and increase the energy consumption.

SUMMARY OF THE PRESENT INVENTION

It is one objective of the present invention to provide a light source apparatus for fluorescence photography, and more particularly to a light source for the fluorescence photography of biomolecule sample gels.

It is another objective of the present invention to provide a light source apparatus for fluorescence photography comprising at least one LED array disposed obliquely out of the range of the light transmissive zone to prevent light spot interference without the use of any diffuser.

It is still another objective of the present invention to provide a light source apparatus for fluorescence photography comprising a transparent plate disposed in the light transmissive zone allowing different exciting lights to pass therethrough.

It is still another objective of the present invention to provide a light source apparatus for fluorescence photography comprising LED arrays of different colors of LEDs to provide different exciting lights for different application requirements.

It is still another objective of the present invention to provide a light source apparatus for fluorescence photography comprising a controller electrically connected to the LED arrays thereof for controlling on/off of every color of LEDs.

It is still another objective of the present invention to provide a light source apparatus for fluorescence photography, wherein the controller can also regulate the brightness of each LED when the LED is turned on.

It is still another objective of the present invention to provide a light source apparatus for fluorescence photography, wherein each LED array comprises a predetermined included angle with the horizontal plane, wherein the predetermined included angle is adjustable for providing different backlight irradiation.

The present invention provides a light source apparatus for fluorescence photography, comprising: a housing having a light transmission zone located on the top thereof; a transparent plate disposed in said light transmission zone of said housing for supporting a biomolecule sample gel; and at least one LED array disposed inside said housing out of the range of said light transmission zone, wherein each of said LED array comprises a plurality of LEDs.

DETAILED DESCRIPTION OF THE PREFERRED EMBODIMENTS

Figure 1:
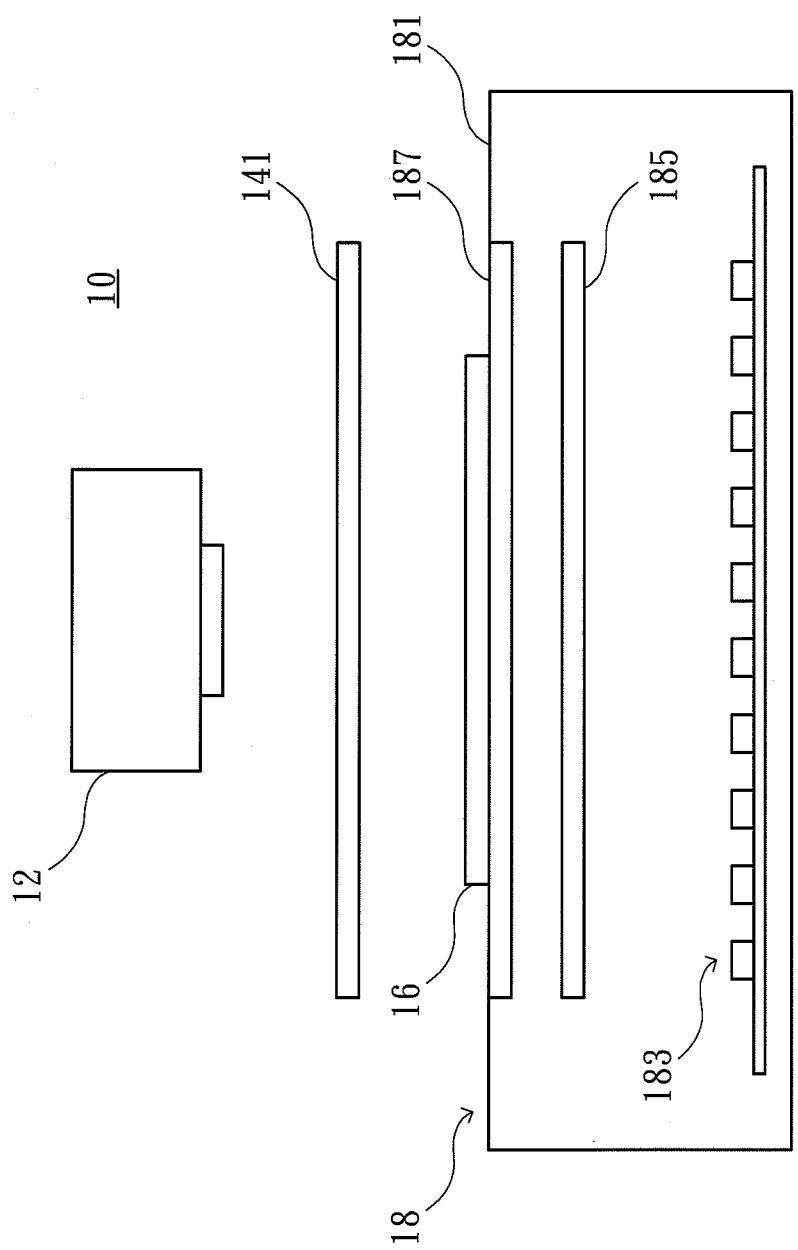
FIG. 1 is a schematic cross-sectional view of a fluorescence photographing apparatus in accordance with a prior art.
Figure 2:
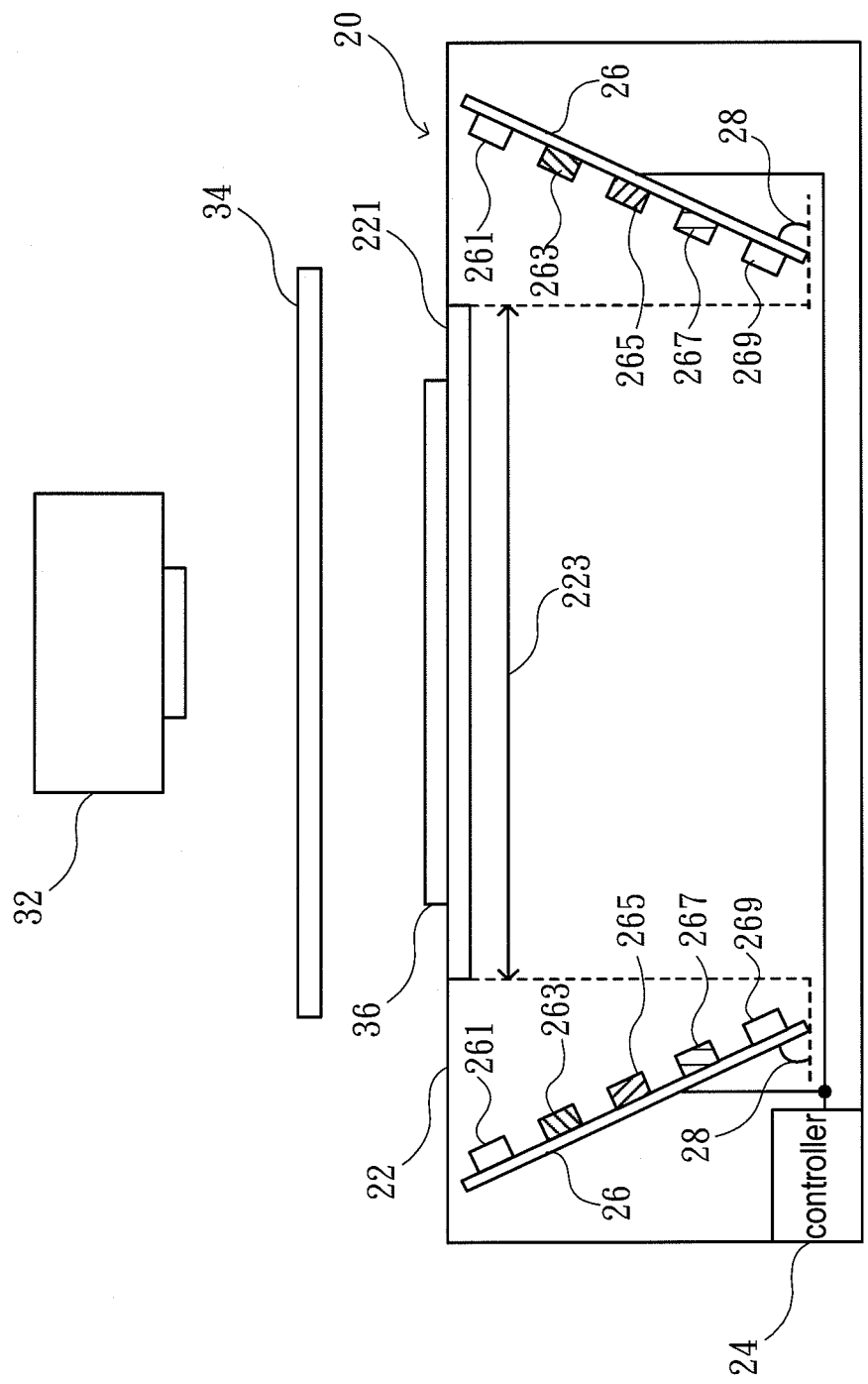
FIG. 2 is a schematic cross-sectional view of a light source apparatus for fluorescence photography in accordance with the present invention.

Referring to FIG. 2, there is shown a light source apparatus 20 for fluorescence photography in accordance with the present invention. The light source apparatus 20 comprises a housing 22, a transparent plate 221 and at least one LED array 26.

The housing 22 has a light transmission zone 223 located on the top thereof. The transparent plate 221 is disposed in the light transmission zone 223 of the housing 22 for supporting a biomolecule sample gel 36. The at least one LED array 26 is disposed inside the housing 22 out of the range of the light transmission zone 223. The exciting light is projected to the light transmission zone 223 and the transparent plate 221 obliquely for preventing the light spots of the LED from interfering in fluorescence photographing or observation.

The transparent plate 221 disposed in the light transmission zone 223 allows different colors of exciting light or ultraviolet light to pass through and irradiate the biomolecule sample gel 36 directly. Therefore, the light source apparatus 20 is suitable for different types of biomolecule samples and enzyme or fluorescent dye. Since the exciting light can be absorbed by the biomolecule sample gel 36 directly without diffusion and filtration, the efficiency is improved. Further, the transparent plate 221 is selected from one of a glass plate or an acryl plate.

The LED array 26 can comprise LEDs of one single color for one single application. Alternatively, the LED array 26 can comprise LEDs of different colors, for example, blue LEDs, green LEDs and UV LEDs (261~269) for multipurpose applications. The light source apparatus 20 can comprise one LED array 26 disposed at one side of the housing 22. Alternatively, the light source apparatus 20 can comprise two LED arrays 26 disposed oppositely at two sides of the housing 22 to provide a uniform irradiation. Moreover, the light source apparatus 20 can comprise a plurality of LED arrays 26 disposed at different sides of the housing 22 for different required irradiation conditions.

Each of the LED arrays 26 comprises a predetermined included angle 28 with the horizontal plane. The predetermined included angle 28 is adjustable for providing different irradiation according to different requirements.

In one embodiment of the present invention, the light source apparatus 20 further comprises a controller 24 electrically connected to the at least one LED array 26 for controlling on/off of every LED, or on/off of every color of LEDs (261~269). The controller 24 can also control the brightness of the LEDs of the at least one LED array 26 when the LEDs are turned on. Further, the predetermined included angle 28 of LED array 26 can also be adjusted by means of the controller 24.

By using the light source apparatus 20 for fluorescence photography of the present invention with a photograph module 32 and a suitable filter 34, the light source apparatus 20 can be used for the fluorescence photographing or observation of different biomolecule sample gels 36, such as protein gel, DNA gel, RNA gel and polysaccharide gel, etc.

Therefore, by using the light source apparatus 20 for fluorescence photography in accordance with the present invention, the application efficiency of the energy resources and material resources are improved.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A light source apparatus for fluorescence photography, comprising:
    a housing having a light transmission zone located on the top thereof;
    a transparent plate disposed in said light transmission zone of said housing for supporting a biomolecule sample gel;
    at least one LED array for fluorescence photography disposed inside said housing, displaced from said light transmission zone, and positioned at a selected oblique angle to project light toward said light transmission zone and said transparent plate, wherein each of said LED array comprises a plurality of LEDs; and
    a controller electrically coupled to said at least one LED array for driving said LED array to said selected oblique angle wherein light spots from said LED array are prevented from interfering with said fluorescence photography.

2. The light source apparatus for fluorescence photography as recited in claim 1, wherein said transparent plate is selected from one of a glass plate or an acrylic plate.

3. The light source apparatus for fluorescence photography as recited in claim 1, wherein each of said LED array comprises at least one color of LEDs.

4. The light source apparatus for fluorescence photography as recited in claim 3, wherein said at least one color of LEDs are selected from one of blue LEDs, green LEDs, ultraviolet LEDs or the combination thereof.

5. The light source apparatus for fluorescence photography as recited in claim 3, further comprising said controller electrically connected to each of said LED array for controlling on/off of each color of LEDs of said LED array.

6. The light source apparatus for fluorescence photography as recited in claim 5, wherein said controller is capable of adjusting the brightness of each color of LEDs when they are turned on.

7. The light source apparatus for fluorescence photography as recited in claim 1, wherein said biomolecule sample gel is selected from one of a protein gel, a DNA gel, an RNA gel or a polysaccharide gel.

* * * * *